US00PP19903P3

(12) United States Plant Patent
Ballington et al.

(10) Patent No.: US PP19,903 P3
(45) Date of Patent: Apr. 14, 2009

(54) BLUEBERRY PLANT NAMED 'CARTERET'

(50) Latin Name: *Vaccinium corymbosum*
Varietal Denomination: Carteret

(76) Inventors: James Ralph Ballington, 260 Kilgore Hall, Horticultural Science Department North Carolina State University, Raleigh, NC (US) 27695-7609; Susan Duke Rooks, Horticultural Crops Research Station, 3800 Castle Hayne Rd., Castle Hayne, NC (US) 28429-6519

( * ) Notice: Subject to any disclaimer, the term of this patent is extended or adjusted under 35 U.S.C. 154(b) by 281 days.

(21) Appl. No.: 11/305,771

(22) Filed: Dec. 19, 2005

(65) Prior Publication Data

US 2007/0143882 P1 Jun. 21, 2007

(51) Int. Cl.
*A01H 5/00* (2006.01)

(52) U.S. Cl. ..... Plt./157
(58) Field of Classification Search ..... Plt./157
See application file for complete search history.

(56) References Cited

U.S. PATENT DOCUMENTS

2007/0130659 P1 * 6/2007 Ballington et al. ..... Plt./157
2007/0143882 P1 * 6/2007 Ballington et al. ..... Plt./157
2007/0143889 P1 * 6/2007 Ballington et al. ..... Plt./203

OTHER PUBLICATIONS

Cline, B. An Overview of Blueberry Releases from NCSU—and other cultivars of Interest for NC Growers pp. 1, 2, 17 and 22, Jun. 2007, Available at:http://www.smallfruits.org/CoAgentTraining/June07Training/ClineCULTIVARREVIEWOPENHOUSE.pdf. http://www.smallfruits.org/CoAgentTraining/Jun.07Training/ClineCULTIVARREVIEWOPENHOUSE.*

* cited by examiner

*Primary Examiner*—Wendy C. Haas

(57) ABSTRACT

*Vaccinium corymbosum* Linnaeus 'Carteret' is a new and distinct variety of blueberry plant that has the following unique combination of desirable features that are outstanding in a new variety.

1. Early-midseason ripening to follow 'Reveille'.
2. Consistent very high yields of small to medium size fruit.
3. Very good picking scar, fruit color and quality.
4. Good fruit firmness and post harvest shelf-life.
5. Adaptation to mechanical harvesting for fresh fruit market outlets.

2 Drawing Sheets

Latin name of the genus and species: The Latin name of the novel blueberry plant variety disclosed herein is *Vaccinium corymbosum* Linnaeus.

Variety denomination: The inventive cultivar of *Vaccinium corymbosum* plant disclosed herein has been given the variety denomination 'Carteret'.

BACKGROUND OF THE INVENTION

The present invention relates to a new and distinct cultivar of *Vaccinium corymbosum* Linnaeus plant (blueberry) grown as a fruiting woody shrub for commercial agriculture. Blueberries are typically consumed both fresh and in a number of processed products.

The new and distinct variety of blueberry plant (*Vaccinium corymbosum* Linnaeus) originated from the hand pollinated cross of 'Bounty' (unpatented)×NC 2426 (unpatented) made in 1980 in Raleigh, N.C.

Seeds from this hand pollination were germinated in winter 1980/1981 in Raleigh, N.C., and 100 seedlings were established in a Fuquay soil amended with pine bark at Jackson Springs, N.C., in 1982. When the seedlings reached maturity in 1987, an elite genotype designated as NC 2925 was selected for its vigorous erect plant habit and superior productivity, color, picking scar, firmness and quality by James R. Ballington. Fruit firmness appeared sufficient that this genotype might be adapted to mechanical harvesting for fresh market outlets. It also possessed another attribute essential for adaptation to mechanical harvest for the fresh market, small to medium fruit size.

During 1988 the original seedling of NC 2925 was propagated by hardwood stem cuttings under intermittent mist in a greenhouse in Raleigh, N.C., and following rooting, single three plant plots were established at Castle Hayne and Jackson Springs, N.C., in 1989. Based on its performance in these initial trials, in 1996 it was propagated again by hardwood and softwood stem cuttings at Castle Hayne, N.C., and also established in replicated trials at Castle Hayne. It was also established in grower trials at Harrells, Ivanhoe, Rocky Point and White Lake, N.C., and at Clarksville, Ariz., in 2001, all under Memoranda of Agreements whereby the growers provided the land and care of the plants but were not granted ownership rights to the variety. Based on performance in the replicated and grower trials it was determined that NC 2925 was worthy of release as a new blueberry cultivar. Plants and fruit of this new variety have remained true to type through successive cycles of asexual propagation by hardwood and softwood stem cuttings at Raleigh and Castle Hayne, N.C. This new variety has been named the 'Carteret' cultivar.

SUMMARY OF THE INVENTION

'Carteret' is a new and distinct variety of blueberry plant that is adapted to mechanical harvest for the fresh market. It has very high yield potential, very good fruit quality and fruit color, an excellent picking scar and modest fruit size which is a requirement for adaptation to mechanical harvest for the fresh market in North Carolina. Fruit firmness was also sufficient for mechanical harvest for the fresh market. Post harvest shelf-life was equal to current named fresh market mechanical harvest adapted to varieties when stored at 70° F. for seven days. Plants are vigorous and plant habit upright. Leaves are elliptic-obovate to elliptic in shape, both the leaf base and apex angles are acute, and the apical third of the leaf margin is occasionally irregularly serrulate. The flowers are self-fertile and produce abundant pollen. 'Carteret' averaged 5.5 flowers per inflorescence, and the corolla is cylindro-urceolate in shape. The fruit is round-oblate in shape and the calyx prominent and held perpendicular to the fruit. The fruit ripens in early midseason. The 'Carteret' plant is equal to vigor to 'Reveille' and 'Lenoir', but not quite as vigorous as 'Beaufort'. 'Carteret' is readily asexually propagated by either softwood or hardwood stem cuttings. It has not had any problems to date with either stem canker or stem blight, the two major diseases of commercial blueberries in North Carolina.

With regard to consistent differences between 'Carteret' and all four of the other varieties with which it was compared, the stem internode length of 'Carteret' was longer than 'Beaufort', and especially 'Reveille', 'Pamlico' and 'Lenoir'. The apical third of the leaf margins on 'Carteret' were occasionally irregularly serrulate while the leaf margins on 'Beaufort', 'Reveille', 'Pamlico', and 'Lenoir' were always completely entire. The length to width ratio of leaves of 'Carteret' was 1.74 and less than 'Lenoir' (1.85), 'Reveille' (2.20), 'Beaufort' (2.28), and 'Pamlico' (2.73). Average fruit yield was also higher than the other four varieties. The fruit calyces on 'Carteret' and 'Pamlico' were protruding and prominent, however they were more prominent on 'Carteret'. Fruit calyces on 'Beaufort', 'Lenoir' and 'Reveille' were appressed and not prominent.

BRIEF DESCRIPTION OF THE DRAWINGS

The photographs in the drawings were made using digital photography techniques, and illustrate the colors as true as reasonably possible when using these techniques. Colors in the photographs may differ slightly from the color values cited in the detailed botanical description, which accurately describe the colors of the new *Vaccinium corymbosum* plant variety. All photographs were taken from plants growing at Castle Hayne, N.C.

FIG. 1 shows the typical plant habit of 'Carteret'.

FIG. 2 shows the typical fruit of 'Carteret'.

DETAILED BOTANICAL DESCRIPTION OF THE VARIETY

The following is a detailed botanical description of a new and distinct variety of *Vaccinium corymbosum* Linnaeus plant known as 'Carteret'. The observations below are from mature plants grown in test plots at a standard commercial spacing of 4' between plants in rows and 10' between rows, at Castle Hayne, N.C. Those skilled in the art of cultivar description and evaluation will appreciate that certain characteristics of a variety will vary with older or, conversely, with younger plants. 'Carteret' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length and cultural conditions. Color notations are based on the Royal Horticultural Society Colour Chart, The Royal Horticultural Society, London, UK, 1995 edition.

For botanical description purposes, 'Carteret' was compared to the early ripening fresh market mechanical harvest adapted cultivar 'Reveille' (unpatented) and to three recent fresh market mechanical harvest adapted cultivars 'Beaufort' (U.S. Plant Pat. Publication No. 20070143889), 'Lenoir' (unpatented) and 'Pamlico' (unpatented). The botanical descriptive data presented are averages of data collected from mature nine year old plants growing in a replicated trial at Castle Hayne, N.C., in 2005. The exception to using average values was with seed numbers where these were determined from a representative fruit of each cultivar.

Plant:

Dimensions:

*Carteret.*—1.4 m height, 1.1 m diameter, H/D ratio 1.27.

*Reveille.*—1.4 m height, 1.2 m diameter, H/D ratio 1.17.

*Pamlico.*—1.3 m height, 1.2 m diameter, H/D ratio 1.08.

*Lenoir.*—1.4 m height, 1.2 m diameter, H/D ratio 1.17.

*Beaufort.*—1.4 m height, 1.1 m diameter, H/D ratio 1.27.

Growth habit: Upright for Carteret, Reveille, Lenoir and Beaufort. Semi-upright for Pamlico.

Mature cane diameter:

*Carteret.*—4.4 cm.

*Reveille.*—4.4 cm.

*Pamlico.*—3.1 cm.

*Lenoir.*—4.2 cm.

*Beaufort.*—3.2 cm.

Mature cane length:

*Carteret.*—1.1 m.

*Reveille.*—1.1 m.

*Pamlico.*—1.0 m.

*Lenoir.*—1.1 m.

*Beaufort.*—1.1 m.

Vigor-average annual growth per new cane:

*Carteret.*—34 cm.

*Reveille.*—35 cm.

*Pamlico.*—30 cm.

*Lenoir.*—33 cm.

*Beaufort.*—40 cm.

Internode length on first flush growth:

*Carteret.*—13.0 cm.

*Reveille.*—7.5 cm.

*Pamlico.*—8.0 cm.

*Lenoir.*—9.0 cm.

*Beaufort.*—10.0 cm.

Number of renewal stems:

*Carteret.*—1.0.

*Reveille.*—0.5.

*Pamlico.*—2.0.

*Lenoir.*—2.0.

*Beaufort.*—1.0.

Dormant mature stem color: Gray-brown (RHS 199C) for Carteret, Reveille, Pamlico and Beaufort. Gray-brown (RHS 199C–199D) for Lenoir.

Dormant one year stem color:

*Carteret.*—red (RHS 46A) on all surfaces.

*Reveille.*—Red (RHS 46A) on all surfaces.

*Pamlico.*—Red (RHS 46B) on the exposed surface, yellow-green (RHS 146C) on the unexposed surface.

*Lenoir.*—Red (RHS 46A) on the exposed surface, yellow-green (RHS 146C–147C) on the unexposed surface.

*Beaufort.*—Red (RHS 46A) on the exposed surface, yellow-orange (RHS 22A) on the unexposed surface.

First flush growth stem color in summer:

*Carteret.*—Yellow-green (RHS 145A).

*Reveille.*—Green (RHS 138C).

*Pamlico.*—Yellow-green (RHS 145B).

*Lenoir.*—Yellow-green (RHS 147C).

*Beaufort.*—Yellow-green (RHS 145B).

Pubescence on summer and one year dormant stems: No stem pubescence on Carteret, Reveille, Pamlico, Lenoir, or Beaufort.

Leaves:

Leaf blade dimensions:

*Carteret.*—Length 61 mm, width 35 mm, L/W ratio 1.74.

*Reveille.*—Length 44 mm, width 20 mm, L/W ratio 2.20.

*Pamlico.*—Length 60 mm, width 22 mm, L/W ratio 2.73.

*Lenoir.*—Length 61 mm, width 33 mm, L/W ratio 1.85.

*Beaufort.*—Length 66 mm, width 29 mm, L/W ratio 2.28.

Leaf petiole length:

*Carteret.*—4 mm.

*Reveille.*—2 mm.

*Pamlico.*—4 mm.

*Lenoir.*—3 mm.

*Beaufort.*—4 mm.

Leaf shape:

*Carteret.*—Elliptic-obovate to elliptic.

*Reveille.*—Narrowly elliptic to narrowly elliptic-obovate.

*Pamlico.*—Narrowly elliptic.

*Lenoir.*—Elliptic to elliptic obovate.

*Beaufort.*—Narrowly elliptic.

Leaf apex angle: Acute for Carteret, Reveille, Pamlico and Beaufort. Acuminate for Lenoir.

Leaf base angle: Acute for Carteret, Reveille, Pamlico, Lenoir and Beaufort.

Leaf margin: Mainly entire, but with occasional irregular serrulations for Carteret. Entire for Reveille, Pamlico, Lenoir and Beaufort.

Leaf pubescence: None for Carteret, Reveille, Pamlico, Lenoir and Beaufort.

Leaf glands: None for Carteret, Reveille, Pamlico, Lenoir and Beaufort.

Leaf color: The adaxial leaf surface color is green (RHS 137A–137B) and the abaxial surface color also green (RHS 138B) for Carteret and Pamlico. The adaxial surface color is green (RHS 137A) and the abaxial color green (RHS 138B) for Lenoir. The adaxial surface color is green (RHS 139A) and the abaxial color green (RHS 138C) for Reveille and Beaufort.

Flowers:

Number of petals: Five, fused into a corolla tube.

Number of flowers per inflorescence:

*Carteret.*—5.5.

*Reveille.*—4.0.

*Pamlico.*—4.0.

*Lenoir.*—5.0.

*Beaufort.*—3.0.

Flower dimensions: Carteret, Pamlico, Lenoir and Beaufort-length 9.0 mm, diameter 5.0 mm, L/D ratio 1.8.

*Reveille.*—Length 9.0 mm, diameter 7.0 mm, L/D ratio 1.3.

Length of the single style:

*Carteret and beaufort.*—8.0 mm.

*Reveille, pamlico and lenoir.*—9.0 mm.

Flower shape:

*Carteret, pamlico, lenoir and beaufort.*—Cylindro-urceolate.

*Reveille.*—Urceolate.

Flower color:

*Carteret.*—Red-purple (RHS 73C) on the fused petal lobes just prior to opening, fading to all white (RHS 155D) on fully open flowers.

*Reveille.*—Red-purple (RHS 63B) on the exposed side and all lobes of the flowers just prior to opening, fading to all white (RHS 155B) on fully open flowers.

*Pamlico.*—Red-purple (RHS 62D) on the basal half of the flowers just prior to opening, fading to all white (RHS 155D) on fully open flowers.

*Lenoir.*—Red-purple (RHS 62C) on the basal half of flowers just prior to opening, fading to all white (RHS 155C) on fully open flowers.

*Beaufort.*—White (RHS 155D) just prior to opening and on fully open flowers.

Fruit:

Fruit dimensions:

*Carteret.*—Length 15 mm, diameter 18 mm, L/D ratio 0.83.

*Reveille.*—Length 15 mm, diameter 16 mm, L/D ratio 0.94.

*Pamlico.*—Length 13 mm, diameter 15 mm, L/D ratio 0.87.

*Lenoir.*—Length 12 mm, diameter 17 mm, L/D ratio 0.71.

*Beaufort.*—Length 13 mm, diameter 16 mm, L/D ratio 0.81.

Fruit shape:

*Carteret.*—Round-oblate.

*Reveille.*—Round.

*Pamlico.*—Round-oblate.

*Lenoir.*—Oblate.

*Beaufort.*—Round-oblate.

Fruit pedicel length:

*Carteret.*—4 m.

*Reveille.*—4 mm.

*Pamlico.*—6 mm.

*Lenoir.*—8 mm.

*Beaufort.*—7 mm.

Fruit picking scar:

*Carteret.*—1.0 mm diameter, dry.

*Reveille.*—1.0 mm diameter, dry.

*Pamlico.*—1.0 mm diameter, dry.

*Lenoir.*—2.0 mm diameter, dry.

*Beaufort.*—1.5 mm diameter, dry.

Fruit calyx orientation and prominence: Perpendicular (protruding) and prominent for Carteret and Pamlico.

Appressed against the apical end of the fruit and not prominent for Reveille, Lenoir and Beaufort.

Fruit color with bloom (epicuticular wax):

*Carteret.*—Violet-blue (RHS 97C) (FIG. 2).

*Reveille.*—Violet-blue (RHS 97B–97C)).

*Pamlico.*—Violet-blue (RHS 97D).

*Lenoir.*—Violet-blue (RHS 97B).

*Beaufort.*—Violet-blue (RHS 97C).

Fruit color without bloom: Black (RHS 202A) for Carteret, Reveille, Pamlico, Lenoir and Beaufort.

Seeds:

Number of fully developed seeds per berry:

*Carteret.*—32.

*Reveille.*—36.

*Pamlico.*—29.

*Lenoir.*—22.

*Beaufort.*—44.

Seed dimensions:

*Carteret.*—Length 1.50 mm, width 1.00 mm, L/W ratio 1.5.

*Reveille.*—Length 1.25 mm, width 1.00 mm, L/W ratio 1.2.

*Pamlico.*—Length 1.50 mm, width 1.00 mm, L/W ratio 1.5.

*Lenoir.*—Length 1.50 mm, width 0.75 mm, L/W ratio 2.0.

*Beaufort.*—Length 1.25 mm, width 1.00 mm, L/W ratio 1.2.

Seed shape:

*Basically depressed.*—Ovate for Carteret, Reveille, Pamlico, Lenoir and Beaufort.

The technical (pomological) descriptive data comparing 'Carteret' to 'Reveille', 'Pamlico', 'Lenoir' and 'Beaufort' at Castle Hayne, N.C., is presented in Tables 2–7, except for time of flowering, where the data was more representative from Jackson Springs, N.C., in 1992 (Table 1).

Time of flowering: Carteret was very similar to Pamlico for dates of first bloom and 50% bloom (Table 1). It was also similar to Reveille and Beaufort for date of first bloom, but about 9 days earlier for date of 50% bloom. It was 11 days earlier than Lenoir for date of first bloom and 10 days earlier for date of 50% bloom.

TABLE 1

Time of flowering of blueberry cultivars at Jackson Springs, NC, in 1992.

| Cultivar | Date of first bloom | Date of 50% bloom |
|---|---|---|
| Carteret | 3/12 | 4/1 |
| Reveille | 3/12 | 4/9 |
| Pamlico | 3/12 | 4/3 |
| Lenoir | 3/23 | 4/11 |
| Beaufort | 3/12 | 4/10 |

Pollination requirements: The flowers of Carteret are self-fertile.

Pollen production: Carteret flowers produce abundant pollen.

Season of ripening: With regard to ripening season, Carteret ripened in the same season as Pamlico and Lenoir at Castle Hayne, N.C. (Table 2). It was later than Reveille and earlier than Beaufort. Carteret is a good variety to interplant with Lenoir. It ripens with the latter variety and overlaps sufficiently in bloom with it to provide cross-pollination (Table 1) since Lenoir is not self-fertile.

TABLE 2

Season of ripening for blueberry cultivars at Castle Hayne, NC.

| | Cumulative percent ripe by June eighth[1] | | | |
|---|---|---|---|---|
| Cultivar | 1999 | 2000 | 2001 | Average |
| Carteret | 38 | 74 | 43 | 52 |
| Reveille | 79 | 100 | 91 | 90 |
| Pamlico | 38 | 74 | 43 | 52 |
| Lenoir | 38 | 70 | 43 | 50 |
| Beaufort | 29 | 55 | 33 | 39 |

[1]Percent ripe after the first two weeks of the season.

Yield per plant: Yield of Carteret was excellent, it was significantly higher than the other four varieties in 1999 (Table 3). It was also higher in 2001, but not significantly higher than Pamlico and Lenoir. Yield was not representative in 2000 because the harvest method (catch frames and rubber hoses) resulted in a high percentage of fruit falling to the ground rather than into the catch frames. The overall average yield of Carteret was also higher than the other four varieties.

TABLE 3

Yield of blueberry cultivars at Castle Hayne, NC.

| | Yield (lbs./plant)[1] | | | |
|---|---|---|---|---|
| Cultivar | 1999 | 2000[2] | 2001 | Average |
| Carteret | 14.0a | 3.3bc | 14.3a | 10.5 |
| Reveille | 5.9cd | 2.4c | 8.8c | 5.7 |
| Pamlico | 7.7bcd | 4.6a | 11.6ab | 8.0 |
| Lenoir | 5.9cd | 4.4ab | 12.5ab | 7.6 |
| Beaufort | 8.6bc | 3.3bc | 10.8bc | 7.5 |

[1]Values not followed by the same letter(s) are significantly different at the 0.05 level (Duncan's Multiple Range Test).
[2]Yield adversely affected by harvest method (catch frames and rubber hoses).

Fruit size (weight per berry): There were few differences between Carteret and the other four varieties for fruit size (Table 4). This is not surprising since all were originally selected for adaptation to mechanical harvest for the fresh market, which dictates that the fruit size be modest to minimize damage to the fruit during the harvesting process.

TABLE 4

Fruit size of blueberry cultivars at Castle Hayne, NC.

| | Fruit size (weight per berry in grams)[1] | | | |
|---|---|---|---|---|
| Cultivar | 1999 | 2000 | 2001 | Average |
| Carteret | 1.22 | 1.30 | 1.15abc | 1.22 |
| Reveille | 1.31 | 1.27 | 1.14abc | 1.24 |
| Pamlico | 1.27 | 1.25 | 0.96cd | 1.16 |
| Lenoir | 1.34 | 1.22 | 1.12bc | 1.23 |
| Beaufort | 1.26 | 1.27 | 1.10bcd | 1.21 |

[1]Values not followed by the same letter(s) are significantly different at the 0.05 level (Duncan's Multiple Range Test).

Fruit color: In addition to the Royal Horticultural Society Colour Chart, fruit color was also determined objectively with a Minolta Color Meter (Table 5), and these data indicated that Carteret was equal to all varieties with which it was compared except Pamlico.

TABLE 5

Fruit color and fruit firmness of blueberry cultivars at Castle Hayne, NC.

| | Color[1,2] | Firmness[1,3] | |
|---|---|---|---|
| Cultivar | 2001 | 1999 | 2001 |
| Carteret | 18.1cd | 118c | 144d |
| Reveille | 20.2abc | 173a | 216a |
| Pamlico | 22.6a | 124c | 172c |
| Lenoir | 14.1d | 124c | 176bc |
| Beaufort | 18.8bc | 142b | 190b |

[1]Values not followed by the same letter(s) are significantly different at the 0.05 level (Duncan's Multiple Range Test).
[2]Color (lightness or "L" values) determined objectively by a Minolta Color Meter. Higher values indicate lighter blue color.
[3]Fruit firmness determined objectively using a Firm-tech Firmness Tester.

Fruit firmness: Fruit firmness determined by a Firm-tech Firmness Tester demonstrated that Carteret was equal to Pamlico and Lenoir, but inferior to Reveille and Beaufort in 1999 (Table 5). It was inferior to all the other varieties for fruit firmness in 2001, however, it was still firm enough to mechanically harvest for the fresh market.

Fruit favor: Subjective ratings for flavor indicated that Carteret was equal to Reveille and Beaufort in 1999 and superior to Pamlico and Lenoir (Table 6). It was only a 72 for flavor in 2000, which indicates that fruit quality may have been more adversely affected by the rubber hose fruit removal system than the other varieties. Carteret was equal to all varieties but Reveille for flavor in 2001.

TABLE 6

Fruit flavor of blueberry cultivars at Castle Hayne, NC.

| | Flavor[1,2] | | |
|---|---|---|---|
| Cultivar | 1999 | 2000 | 2001 |
| Carteret | 79a | 72f | 78bc |
| Reveille | 80a | 79a | 80a |
| Pamlico | 76b | 74e | 79ab |
| Lenoir | 75b | 76bcd | 79ab |
| Beaufort | 80a | 78ab | 79ab |

[1]Values not followed by the same letter(s) are significantly different at the 0.05 level (Duncan's Multiple Range Test).
[2]Subjective ratings based on a 0-90 scale, where less than 60 is unsatisfactory, 60-69 is satisfactory, 70-79 is average to good, and 80 and above superior.

Post harvest shelf-life: Carteret was not equal to Reveille, Pamlico and Lenoir for percent marketable fruit after seven days storage at 50° F. (Table 7). It was equal to these three varieties when held at 70° F. for seven days. Carteret was superior to Beaufort for post harvest shelf-life at both temperatures.

TABLE 7

Post harvest shelf-life of the fruit of blueberry cultivars at Castle Hayne, NC, in 2001.

| | Percent marketable fruit after seven days[1] | |
|---|---|---|
| Cultivar | 50° F. | 70° F. |
| Carteret | 62b | 44a |
| Reveille | 81a | 48a |
| Pamlico | 77a | 38a |
| Lenoir | 83a | 44a |
| Beaufort | 52c | 8b |

[1]Values not followed by the same letter(s) are significantly different at the 0.05 level (Duncan's Multiple Range Test).

Propagation: Carteret is easily propagated asexually by both hardwood and softwood stem cuttings.

Disease reaction: Carteret has not had any problems with either of the two major diseases affecting blueberries in North Carolina, stem canker (*Botryosphaeria corticis*) and stem blight (*Botryospheria dothidea*).

That which is claimed is:

1. A new and distinct variety of commercial blueberry plant (*Vaccinium corymbosum Linnaeus*) substantially as illustrated and described, characterized by its early-midseason ripening, very high yields, very good picking scar, fruit quality, and color, good firmness and post harvest shelf-life, small to medium fruit size, and adaptation to mechanical harvest for fresh fruit market outlets.

* * * * *

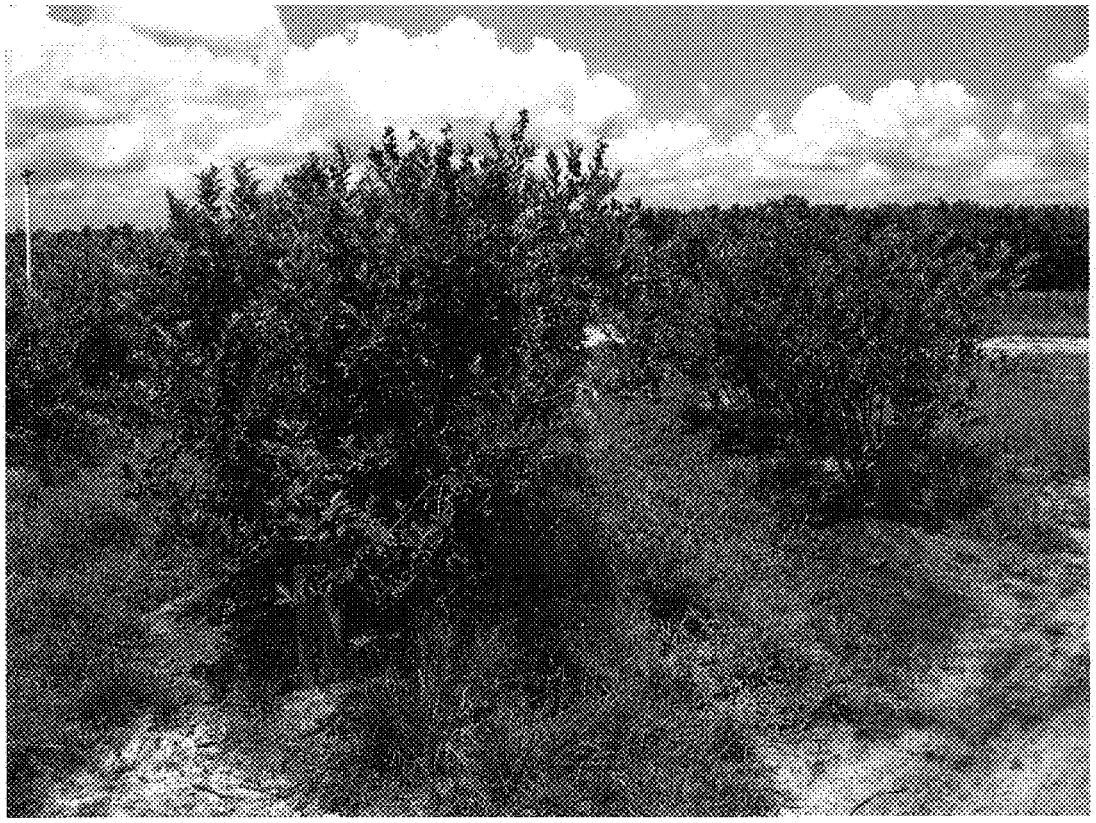
FIG. 1. CARTERET PLANT HABIT

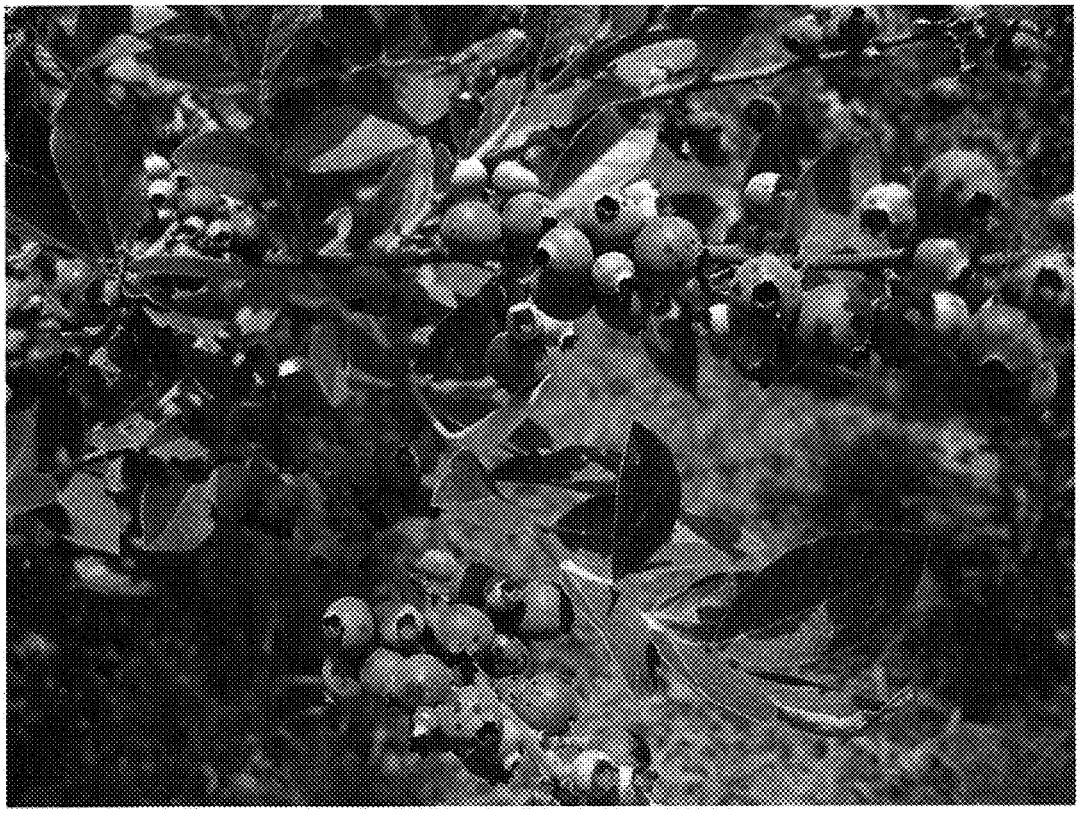
FIG. 2. CARTERET FRUIT